United States Patent [19]

Heggie et al.

[11] Patent Number: 4,863,639

[45] Date of Patent: Sep. 5, 1989

[54] APPLICATION OF CATALYSTS CONTAINING RHODIUM

[75] Inventors: William Heggie, Barreiro; Philip R. Page, Sintra; Ivan Villax, Lisboa Codex, all of Portugal; Michael Hursthouse, Chelmsford; Richard Somerville, Hornchurch, both of England

[73] Assignee: Plurichemie Anstalt, Vaduz, Liechtenstein

[21] Appl. No.: 50,931

[22] Filed: May 15, 1987

[30] Foreign Application Priority Data

Mar. 25, 1987 [PT] Portugal .............................. 74303[U]

[51] Int. Cl.$^4$ ........................................... C07C 103/19
[52] U.S. Cl. ................................. 260/351.5; 502/166
[58] Field of Search ...................... 502/166; 260/351.5

[56] References Cited

U.S. PATENT DOCUMENTS

| 4,500,458 | 2/1985 | Villax et al. | ...................... 260/351.5 |
| 4,550,096 | 10/1985 | Page et al. | ......................... 260/351.5 |
| 4,743,699 | 5/1988 | Page et al. | ......................... 260/351.5 |

Primary Examiner—Richard L. Raymond
Assistant Examiner—Raymond Covington
Attorney, Agent, or Firm—Ostrolenk, Faber, Gerb & Soffen

[57] ABSTRACT

The present invention refers to the compounds ($\mu$-hydrazine-$N^1$:$N^2$)-bis[bis(triphenylphosphine)-chlororhodium (I)] and di($\mu$-hydrazine-$N^1$:$N^2$)-bis[bis(triphenylphosphine)rhodium (I)] dichloride, which are homogenous hydrogenation catalysts and their application in the hydrogenation of the exocyclic methylene group of acid addition salts of 6-demethyl-6-deoxy-6-methylene-5-hydroxytetracycline (methacycline) to prepare $\alpha$-6-deoxy-5-hydroxytetracycline (doxycycline).

4 Claims, No Drawings

APPLICATION OF CATALYSTS CONTAINING RHODIUM

The present invention refers to the compounds (μ-hydrazine-N¹:N²)-bis[bis(triphenylphosphine)-chlororhodium (I)] and di(μ-hydrazine-N¹:N²)-bis[bis(triphenylphosphine)rhodium (I)]dichloride, which are homogenous hydrogenation catalysts and their application in the hydrogenation of the exocyclic methylene group of acid addition salts of 6-demethyl-6-deoxy-6-methylene-5-hydroxytetracycline (methacycline) to prepare α-6-deoxy-5-hydroxytetracycline (doxycycline).

Doxycycline is a wide-spectrum antibacterial agent, with widespread application in the treatment of numerous infections in humans and in animals. The hydrogenation of the exocyclic methylene group of methacycline can produce two epimers. The α-6-epimer is doxycycline, whilst the β-6-epimer, called 6-epi-doxycycline, is devoid of clincal utility. Thus, it is important that the hydrogenation does not co-produce this β-6-epimer. In fact, the British Pharmacopoeia 1980 established a limit for the content of 6-epi-doxycycline in doxycycline of 2%.

In the prior art, doxycycline was first described in 1960 in U.S. Pat. No. 3,200,149. Since that time many methods have been described for the preparation, in all of which the modification of the catalytic system has been described as producing improved yields or a purer product. In the field of heterogenous catalysis, U.S. Pat. Nos. 3,444,198, 3,849,491, 3,954,862 and 4,597,904 and the report in Chemical Abstracts 86, 89476 f (1977) of Hungarian Pat. No. 12,042 have all taught improved methods for the preparation of doxycycline and its analogues.

The first use of homogenous catalysis was described in U.S. Pat. No. 4,207,258 (Italian priority 1972), wherein the catalyst was a complex of rhodium with tertiary phosphine, arsine and stibine ligands. U.S. Pat. No. 3,962,331 extended the above process to the simultaneous reductive dehalogenation and hydrogenation of an 11a-halomethacycline. French Pat. No. 2,216,268 later disclosed the use of the same catalyst.

Since that time, other patents have appeared such as U.S. Pat. Nos. 3,907,890, 4,001,321 and 3,962,131 all describing variations in the catalytic system and claiming improved yields and stereospecificity.

The first homogenous hydrogenation catalysts of the type of tertiary phosphine-hydrazino-rhodium complexes were described in U.S. Pat. No. 4,550,096. These were prepared by reacting a rhodium salt, specifically rhodium trichloride, with a tertiary phosphine and a hydrazine or by reacting a rhodium complex, such as tris(triphenylphosphine)chlororhodium, with a hydrazine. These complexes allowed the preparation of doxycycline, containing less than 1% of the undesired 6-epi-doxycycline, in high yield using considerably less rhodium than had been taught in the prior art.

These complexes have proved to be very satisfactory catalysts for the hydrogenation of methacycline especially if an excess of a tertiary phosphine is included in the hydrogenation mixture as a promoter.

The exact chemical formulae and structures of the catalysts of this U.S. Patent were not disclosed in the patent, but reported elemental analyses showed some significant variability in elemental composition indicating variations in constitution.

It has now been found that, by changing the process conditions used in the U.S. Patent, very satisfactory new catalysts can be made which have well defined structures. It is advantageous, from general considerations, to be able to use catalysts of precisely known formula and structure, and furthermore the new catalysts are very effective for the hydrogenation of methacycline without the need to add any excess tertiary phosphine.

According to the present invention, there is provided a process for the preparation of a complex of rhodium and hydrazine, containing triphenylphosphine and chlorine, useful as a homogeneous hydrogenation catalyst, which comprises reacting tris(triphenylphosphine)chlororhodium with hydrazine or hydrazine hydrate in methanol under an inert atmosphere, stirring the reaction mixture at room temperature, or refluxing it and then recovering the solid complex from the mixture, characterised in that the reaction is conducted in the absence of oxygen using degassed methanol, and wherein either (a) a complex of formula I:

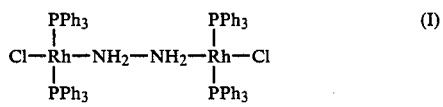

wherein Ph is phenyl, is obtained when each mole of tris(triphenylphosphine)chlororhodium is reacted with at least one half of a mole of hydrazine with stirring at room temperature until precipitation thereof from the mixture, or (b) a complex of formula II:

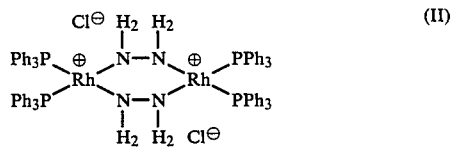

wherein Ph is phenyl, is obtained when for each mole of tris(triphenylphosphine)chlororhodium at least one mole of hydrazine is used, and the reaction mixture is stirred at room temperature for a prolonged period or refluxed, followed by standing at room temperature for at least 12 hours in order to form crystals of the complex.

The invention includes the new catalyst compounds of formula I and formula II per se, and also a process for the catalytic stereospecific hydrogenation of an acid addition salt of 6-demethyl-6-deoxy-6-methylene-5-hydroxytetracycline to prepare α-6-deoxy-5-hydroxytetracycline, wherein the hydrogenation is carried out at a temperature between 60° C. and 100° C., at a pressure of 1 to 10 kg/cm² until the reaction is complete, followed by isolation of the thus formed compound by known processes, charaterised by using a catalyst prepared by the process of the invention.

In the process of the invention for making the new catalysts, the tris(triphenylphosphine)chlororhodium must be freshly prepared, and stored and manipulated under an inert atmosphere. The preparation and isolation of the complexes must be carried out under an inert atmosphere with complete exclusion of air and in degassed reaction media, followed by drying under an inert atmosphere or in vacuum. After eventual purification, the complexes obtained are of a uniform composition and well defined formulae, being novel compounds, never previously described.

According to the present invention, a catalyst of the formula I is obtained by reacting, under an inert atmosphere at room temperature for up to four hours, one mole of tris(triphenylphosphine)chlororhodium with at least half a mole of hydrazine in degassed methanol, followed by isolation and drying under an inert atmosphere or vacuum.

The same reaction can be carried out, with the same precautions as to the exclusion of air, at room temperature for a prolonged period or at reflux, followed by standing at room temperature for at least 12 hours, for example one to two days, with at least one mole of hydrazine, giving crystals of the catalyst of the formula II.

Both formulae have been unequivocally established by elemental analysis, as well as by infra-red and nuclear magnetic resonance spectroscopy, and in the second case by X-ray crystallography.

It is to be noted that both of these structures fall within the general structure given in U.S. Pat. No. 4,550,096.

The catalysts when prepared according to the conditions described above, are fully active in the hydrogenation of methacycline to doxycycline. Furthermore, it is not necessary to add excess triphenylphosphine to ensure a near stoichiometric yield of the required α-epimer.

The complex bis(triphenylphosphine)hydrazinomethoxyrhodium:

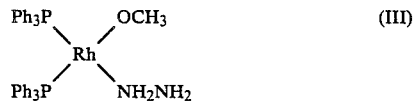

(III)

has been disclosed in European Patent Application No. 85 305 045.8 (Publ. No. 0 187 436). This compound is the result of a side-reaction of the hydrazine and the tris(triphenylphosphine)chlororhodium, with the methanol solvent taking direct part in the reaction.

Thus, the preparation of any one of these three compounds is solely dependant on the physical parameters of the reaction. On this basis, the compounds of structures I and II are in equilibrium in the reaction mixture obtained from the tris(triphenylphosphine)chlororhodium and hydrazine. The precise proportion of each compound is substantially controlled by the physical parameters existing in the mixture.

It is believed that the monomeric structure:

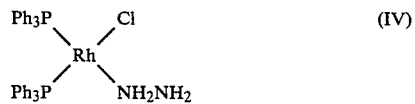

(IV)

is also in equilibrium in the reaction mixture, although this has not been isolated so far.

The conditions of preparation of the catalysts of the present invention are illustrated in Examples 1 and 2. The tris(triphenylphosphine)chlororhodium and hydrazine can be reacted in the molecular proportion corresponding to their respective formulae, but it is advantageous to use hydrazine in excess so as to obtain the maximum yield in relation to the expensive rhodium complex.

The hydrazine can be used as either the anhydrous base or as the monohydrate. It has been verified that the anhydrous base allows shorter reaction times.

To achieve the best results in preparing the compound of formula I, tris(triphenylphosphine)chlororhodium (1 mole) and hydrazine hydrate (3 moles) are mixed in degassed methanol under a nitrogen atmosphere. After stirring for a few hours, the yellow solid precipitates and is filtered and dried under vacuum.

When tris(triphenylphosphine)chlororhodium (1 mole) and hydrazine hydrate (3 moles) are refluxed in degassed methanol under a nitrogen atmosphere, in adequate equipment, followed by standing at room temperature, filtration and drying under vacuum, yellow crystals of the compound of formula II are formed. In contrast, cooling, preferably after concentration, favours the isolation of a yellow solid of formula III.

The complexes of formulae I and II are stable for at least one month, providing they are stored under nitrogen at reduced temperatures. After this period, slightly diminished catalytic activity is sometimes observed. Therefore, these complexes should be in preference freshly prepared to obtain the best hydrogenation results. Alternatively, they can be prepared immediately prior to use and then employed without isolation by addition to the hydrogenation reaction mixture, whereby equally good results can be achieved.

As already indicated, the hydrazino-rhodium complexes of the present invention are efficient homogeneous stereospecific hydrogenation catalysts, in general. The present invention, however, has specifically been directed to their application in the hydrogenation of the exocyclic methylene group of 6-demethyl-6-deoxy-6-methylene-5-hydroxytetracycline present in the hydrogenation reaction mixture as an acid addition salt, so as to yield α-6-deoxy-5-hydroxytetracycline in a near stoichiometric yield.

The starting methacycline can be prepared by any of the known processes, such as that described in U.S. Pat. No. 3,849,491, but should not contain impurities which may act as a catalyst inhibitor.

Although the new complexes will catalyse the hydrogenation of methacycline base, the rate is so slow that the time of hydrogenation does not permit the yields obtained when using an acid addition salt.

The rate of hydrogenation increases with the temperature. Temperatures from ambient to 95° C. can be used, but to achieve the best yields and stereospecificity, the optimum reaction temperature range should be between 85° C. and about 90° C. At 95° C. the yields are slightly lower than for instance at 88° C. Below 85° C., the catalytic system starts to be sensitive to the eventual presence of certain trace impurities which may interfere with the rate of hydrogenation.

In the context of the hydrogenation of methacycline acid addition salts for the preparation of doxycycline, the present invention has several advantages when the temperature range during hydrogenation is 85° C. to about 90° C.

First, there is no necessity for extremely high hydrogen pressures. It has been found that from 1 kg/cm² to 10 kg/cm² will ensure complete conversion of the methacycline substrate in between 6 to about 10 hours. Typically, the hydrogenation is carried out at 88°–89° C. at a hydrogen pressure of 7 to 9 kg/cm² and is complete after 6½ to 7 hours.

Second, the amount of rhodium necessary to obtain complete conversion is of the order of 0.0003 part by weight of rhodium in relation to the methacycline acid addition salt substrate.

The painstaking preparation of the catalysts under strictly inert conditions can be alleviated by their preparation in degassed methanol under a nitrogen atmosphere immediately prior to use, followed by addition to the hydrogenation reaction mixture, after which the actual hydrogenation is carried out.

The transformation of the methacycline acid addition salt into doxycycline using the catalysts of the present invention gives a purity above 95% in the reaction mixture, as analysed by high performance liquid chromatography (h.p.l.c.).

In contrast to the catalysts of U.S. Pat. No. 4,550,096, the catalysts of the present invention when prepared, dried, and stored under a strictly inert atmosphere, exert full activity without the necessity of adding an excess of tertiary phosphine, more specifically triphenylphosphine, to the hydrogenation mixture so as to achieve the best yields.

An explanation for this is that the catalysts prepared according to the process of U.S. Pat. No. 4,550,096

So as to elucidate the behaviour of the triphenylphosphine-hydrazino-chlororhodium catalysts, as well as the actual role of the hydrazine present in the complex, an extensive study on this catalytic system was carried out.

According to U.S. Pat. No. 4,550,096, triphenylphosphine-hydrazino-chlororhodium catalysts can be prepared "in situ" by the addition of rhodium trichloride, triphenylphosphine and hydrazine hydrate to the cold hydrogenation reaction mixture, followed by heating, after which the actual hydrogenation is carried out.

Therefore, a series of parallel hydrogenations was carried out, using methacycline (MOT) hydrochloride in presence of the "in situ" prepared catalyst, in the molar proportion of one mole of rhodium trichloride trihydrate and one mole of triphenylphosphine, without addition of hydrazine hydrate, and with the addition of one and two moles of hydrazine hydrate. Whilst in the absence of hydrazine hydrate, only 60.87% of the $\alpha$-epimer was formed, together with 12.49% of $\beta$-epimer and 14.59% of degradation products, it was verified that in the presence of hydrazine hydrate, the formation of the $\alpha$-epimer increased drastically:

|  | $RhCl_3.3H_2O$ | $Ph_3P$ | $NH_2NH_2.H_2O$ | $\alpha$-epimer % | $\beta$-epimer % | MOT % | Degradation products % |
|---|---|---|---|---|---|---|---|
| Expt. 1 | 1 mole | 1 mole | 0 | 60.87 | 12.44 | 11.74 | 14.95 |
| Expt. 2 | 1 mole | 1 mole | 1 mole | 82.86 | 5.93 | 5.75 | 5.46 |
| Expt. 3 | 1 mole | 1 mole | 2 moles | 92.91 | 2.2 | 4.56 | 0.33 | were believed to be stable and, in fact, they exerted a very high catalytic activity, even when stored for long periods, because they were subsequently employed in presence of a controlled excess of a tertiary phosphine. It is now believed that the catalysts prepared according to the process described in U.S. Pat. No. 4,550,096 oxidise slowly, but the presence of the excess tertiary phosphine in the hydrogenation reaction mixture allowed substitution of the oxidised part of the tertiary phosphine, thereby regenerating the original catalytic system.

As has been previously mentioned, the catalyst is most conveniently prepared immediately prior to use. Thus, hydrazine hydrate (0.5 to 4 moles) is added with stirring to tris(triphenylphosphine)chlororhodium (1 mole) in degassed methanol in a glass vessel, under a nitrogen atmosphere. Upon addition of the hydrazine, the initial red colour turns to yellow. The reaction mixture is stirred for between a few minutes and two hours, and then transferred to the hydrogenator containing the methacycline acid addition salt in methanol at 50° C., under nitrogen.

Subsequently, the reaction vessel is purged again with nitrogen, then with hydrogen, finally being pressurised to 8 kg/cm² with hydrogen. The reaction mixture is heated to 88° C. under stirring, and the temperature maintained at 88° C. ±2° C. until the velocity of consumption of hydrogen slows down drastically, which occurs after about 6 to 7 hours. At this time, the reaction mixture contains nearly exclusively $\alpha$-6-deoxy-5-hydroxytetracycline.

The purity of the reaction mixture thus obtained is such that the doxycycline can be directly crystallised from the reaction mixture by adding excess p-toluenesulphonic acid, followed by cooling, yielding doxycycline p-toluenesulphonate with a purity about 99%.

The new catalysts have been shown to be effectively superior to the Wilkinson catalytic system.

As can be ascertained from these values, the triphenylphosphine-hydrazino-chlororhodium catalytic system contains an active species of only one mole of triphenylphosphine and two moles of hydrazine for each mole-atom of rhodium, which is in contrast with the Wilkinson catalytic system, which must contain at least two moles of triphenylphosphine for each mole-atom of rhodium in order to be efficient.

In parallel hydrogenation experiments with the rhodium-hydrazine catalytic system and the well-known Wilkinson catalyst, using deuterium instead of hydrogen, the products were analysed by mass spectrometry. It has been found that the doxycycline obtained with the hydrazine-containing system contains significantly less deuterium than the doxycycline obtained using the Wilkinson catalyst. This difference indicates that the hydrazine takes an active part in the catalytic hydrogenation.

These results show the positive effect of the hydrazine ligand in the catalytic system of the present invention.

The following examples serve to illustrate the present invention, without in any way limiting the scope thereof.

EXAMPLES (1) Preparation of ($\mu$-hydrazine-$N^1$:$N^2$)-bis[bis(triphenylphosphine)-chlororhodium (I)]

Tris(triphenylphosphine)chlororhodium (0.50 g; 0.54 mmoles) was placed in a two necked round bottom flask. The solid was stirred under vacuum for 30 minutes and then under an atmosphere of nitrogen. Dry, degassed methanol (50 ml) was added and the mixture was stirred for 15 minutes. A methanolic solution of hydrazine hydrate (15 ml of a methanolic solution of hydrazine hydrate containing 5.91 mg/ml; 1.77 mmoles) was added, and the mixture stirred for 3 hours at room temperature. A yellow precipitate formed, which was filtered off and dried under vacuum.

The proton nmr spectrum showed a complex signal centred on δ7.55 (phenyl ring protons) and a broad peak at δ1.8 (hydrazine protons). The infra-red spectrum shows a doublet at 3180 cm$^{-1}$ (N-H stretching), a band at 305 cm$^{-1}$ (Rh-Cl stretching), as well as bands indicative of triphenylphosphine.

Elemental analysis: C: 63.31%, H: 4.81%, N: 2.73%, P: 9.15%. $C_{72}H_{64}Cl_2N_2P_4Rh_2$ requires: C: 63.68%, H: 4.75%, N: 2.06%, P: 9.12%.

A repeat preparation using hydrazine hydrate (1 ml; 20.57 mmoles) gave the same product after stirring at room temperature for 1 hour.

(2) Preparation of di(μ-hydrazine-N$^1$:N$^2$)-bis[bis(triphenylphosphine)rhodium (I)]dichloride:

Tris(triphenylphosphine)chlororhodium (1.05 g; 1.13 mmoles) was placed in a two necked round bottom flask. The solid was stirred under vacuum for 30 minutes and then under an atmosphere of nitrogen. Dry, degassed methanol (170 ml) was added and the mixture was stirred for 15 minutes. A methanolic solution of hydrazine hydrate (30 ml of a methanolic solution containing 5.91 mg/ml; 3.54 mmoles) was added. The reaction mixture was refluxed for 2 hours. Upon standing overnight, yellow crystals were deposited, which were filtered and dried under vacuum.

A single crystal of approximate dimensions 0.3 mm×0.15 mm×0.1 mm was sealed under argon in a thin walled glass capillary. Unit cell and intensity data were obtained using an Enraf-Nonius CAD4 diffractometer, following standard procedures. Details of the experimental features are as follows:

Crystal data: $[C_{72}H_{68}N_4P_4Rh_2].[Cl]_2.CH_3OH$, Mw=1422.02, monoclinic, space group P2$_1$/n, a=15.009(3) Å, b=13.294(2) Å, c=18.391(4) Å, β=108.9(1)°, V=3471.9 Å$^3$, Z=2, Dc=1.36 g.cm$^{-3}$, μ(Mo-Kα)=6.14 cm$^{-1}$.

Data collection: Data were recovered for 1.5°≦θ≦21° at room temperature, 291° K. and corrected for absorption empirically. 3716 intensities were measured, of which 1805 were considered observed [I>1.5 σ(I)] and used in the analysis.

The structure was solved via the heavy atom method and refined by full matrix least squares. In view of the small number of observed data, the structure was refined in the anisotropic approximation, but with the phenyl groups defined as rigid bodies. No hydrogens were confidently located on the hydrazine nitrogen atoms and none were included. The final R value is 0.06.

The complex was found to contain a dimeric cation in which two (Ph$_3$P)$_2$Rh units were linked together by two bridging hydrazine molecules, as shown in II:

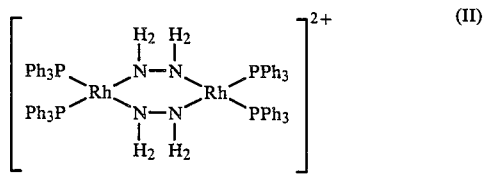

(II)

The rhodium centres have the expected square planar configuration, with the Rh-P and Rh-N distances being normal. The central Rh$_2$N$_4$ ring has a chair conformation, compatible with its centrosymmetric nature.

3. Comparative hydrogenations in presence and absence of hydrazine

A. Molar ratio-Rh:PPh$_3$=1:1

Methacycline hydrochloride (4.0 g; 8.35 mmoles) was suspended in methanol (60 ml) and rhodium trichloride trihydrate (200 mg; 0.75 mmoles) and triphenylphosphine (196.5 mg; 0.75 mmoles) added. The mixture was then hydrogenated for 6 hours at a hydrogen pressure of 8 kg/cm$^2$ and a temperature of 80° C. in a conventional stainless steel high pressure reactor. At the end of the reaction, a sample of the reaction mixture was analysed by h.p.l.c. and gave:

| | |
|---|---|
| α-epimer = | 60.87% |
| β-epimer = | 12.44% |
| methacycline = | 11.74% |
| others = | 14.95% |

B. Molar ratio-Rh:PPh$_3$:NH$_2$NH$_2$=1:1:1

The experiment as described in A above was repeated but with the addition of 0.95 ml of a 0.814M solution of hydrazine hydrate in methanol (0.77 mmoles NH$_2$NH$_2$). H.p.l.c. of the crude reaction mixture gave:

| | |
|---|---|
| α-epimer = | 82.86% |
| β-epimer = | 5.93% |
| methacycline = | 5.75% |
| others = | 5.46% |

C. Molar ratio-Rh:PPh$_3$:NH$_2$NH$_2$=1:1:2

The experiment as described in A above was repeated but with the addition of 1.9 ml of 0.814M solution of hydrazine hydrate in methanol (1.55 mmoles NH$_2$NH$_2$). H.p.l.c. of the crude reaction mixture gave:

| | |
|---|---|
| α-epimer = | 92.91% |
| β-epimer = | 2.2% |
| methacycline = | 4.56% |
| others = | 0.33% |

4. Hydrogenation of methacycline using a non-isolated catalyst:

Tris(triphenylphosphine)chlororhodium (15.0 mg; 0.016 mmoles) and a methanolic solution of hydrazine (124 μl of a 0.4M solution; 0.050 mmoles) were added to methanol (60 ml) in a nitrogen atmosphere with stirring. Methacycline hydrochloride (7.38 g; 15.41 mmoles) was added, and the mixture transferred to a conventional stainless steel high pressure reactor, which was charged to a pressure of 8 kg/cm$^2$ with hydrogen, and then reacted at 88° C. for 6½ hours.

p-Toluenesulphonic acid (3.3 g) was then added and the mixture stirred at 0° C. for 2 hours. The doxycycline p-toluenesulphonate obtained by filtration and drying at 35° C. weighed 8.84 g and had a purity of 98.9%.

5. Hydrogenation of methacycline using (μ-hydrazine-N$^1$:N$^2$)-bis[bis(triphenylphosphine)chlororhodium (I)]

(μ-Hydrazine-N$^1$:N$^2$)-bis[bis(triphenylphosphine)-chlororhodium (I)] (11 mg; 0.0081 mmoles; 0.0162 mmoles of rhodium), as prepared in Example 1, was added to a suspension of methacycline hydrochloride (7.25 g; 15.14 mmoles) in methanol (59 ml) and the mixture hydrogenated at a pressure of 8 kg/cm$^2$ for 6½ hours at 88° C. Thereafter, p-toluenesulphonic acid (3.3 g) was added and the mixture stirred at 0° C. for several hours. The yield of doxycycline p-toluenesulphonate was 8.45 g, 90.5%, which had a purity of 99.0%.

We claim:

1. A process for the catalytic stereospecific hydrogenation of an acid addition salt of 6-demethyl-6-deoxy-6-methylene-5-hydroxytetracycline to prepare α-6-deoxy-5-hydroxytetracycline, wherein the hydrogenation is carried out at a temperature between 60° C. and 100° C., at a pressure of 1 to 10 kg/cm² until the reaction is complete, followed by isolation of the thus formed compound, characterized by using as catalyst a complex of the formula:

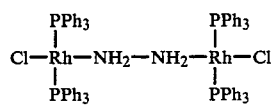  (I)

wherein Ph is phenyl, or a complex of the formula

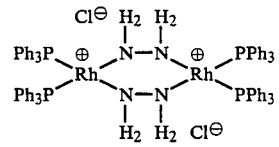  (II)

wherein Ph is phenyl, or a mixture thereof.

2. Process according to claim 1, characterised by the fact that the hydrogenation is carried out at a temperature between 85° C. and about 90° C.

3. A process according to claim 1, wherein the amount of rhodium contained in the catalyst is less than 0.0003 part by weight per part of the 6-demethyl-6-deoxy-6-methylene-5-hydroxytetracycline acid addition salt to be hydrogenated, with the hydrogenation being substantially complete within 10 hours, and the hydrogenation reaction medium is methanol.

4. A process according to claim 2, wherein the amount of rhodium contained in the catalyst is less than 0.0003 part by weight per part of the 6-demethyl-6-deoxy-6-methylene-5-hydroxytetracycline acid addition salt to be hydrogenated, with the hydrogenation being substantially complete within 10 hours, and the hydrogenation reaction medium is methanol.

* * * * *